United States Patent [19]

Ito

[11] Patent Number: 5,472,689

[45] Date of Patent: Dec. 5, 1995

[54] HAIR COSMETIC COMPOSITION CONTAINING A POLY(N-ACYLALKYLENEIMINE)-ORGANOPOLYSILOXANE BLOCK OR GRAFT COPOLYMER

[75] Inventor: Yoshiaki Ito, Chiba, Japan

[73] Assignee: Kao Corporation, Tokyo, Japan

[21] Appl. No.: 915,652

[22] Filed: Jul. 21, 1992

[30] Foreign Application Priority Data

Jul. 22, 1991 [JP] Japan ................... 3-181224

[51] Int. Cl.$^6$ .............. A61K 7/06; A61K 7/11; A61K 47/34
[52] U.S. Cl. ................ 424/70.122; 424/DIG. 2; 252/DIG. 13
[58] Field of Search ............. 424/70, 71, DIG. 2, 424/78.17; 252/DIG. 13; 525/410; 528/28

[56] References Cited

U.S. PATENT DOCUMENTS

| | | | |
|---|---|---|---|
| 4,540,747 | 9/1985 | Saegusa et al. | 524/538 |
| 4,659,777 | 4/1987 | Riffle et al. | 528/14 |
| 4,837,005 | 6/1989 | Brode, II et al. | 424/71 |
| 4,916,195 | 4/1990 | Kanakura et al. | 528/25 |
| 5,087,443 | 2/1992 | Chizat et al. | 424/70 |

OTHER PUBLICATIONS

Chemical Abstracts, vol. 116, No. 18, May 4, 1992, AN 180916y, JP-A 3 287 509, Dec. 18, 1991.
Chemical Abstracts, vol. 114, No. 18, May 6, 1991, AN 165182, JP-A 2 276 824, Nov. 13, 1990.

*Primary Examiner*—Edward J. Webman
*Attorney, Agent, or Firm*—Oblon, Spivak, McClelland, Maier, & Neustadt

[57] ABSTRACT

A hair cosmetic is disclosed, which comprises the following components (a) and (b):

(a) a poly(N-acylalkyleneimine)-modified silicone block or graph copolymer having a poly(N-acylalkyleneimine) segment and an organopolysiloxane segment at a weight ratio of said poly(N-acylalkyleneimine) segment to said organopolysiloxane segment of from 1/20 to 20/1, and having a molecular weight of from 500 to 500,000, wherein said poly(N-acylalkyleneimine) segment comprises a repeating unit represented by the following formula (I):

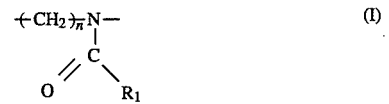

wherein $R_1$ represents a hydrogen atom, an alkyl group having 1 to 22 carbon atoms, a cycloalkyl group having 3 to 22 carbon atoms, an aralkyl group having 7 to 22 carbon atoms or an aryl group having 6 to 22 carbon atoms; and n is 2 or 3; and (b) a film-forming polymer. The hair cosmetic of the present invention is effective in imparting a natural gloss, smoothness, flexibility, smooth-combing properties and water repellency to the hair without deteriorating the hair setting retention function.

13 Claims, No Drawings

HAIR COSMETIC COMPOSITION CONTAINING A POLY(N-ACYLALKYLENEIMINE)-ORGANOPOLYSILOXANE BLOCK OR GRAFT COPOLYMER

FIELD OF THE INVENTION

This invention relates to a hair cosmetic. More particularly, it relates to a hair cosmetic comprising poly(H-acylalkyleneimine)-modified silicone.

BACKGROUND OF THE INVENTION

Various polymers have been widely employed in order to impart a good feel to hair cosmetics. These polymers are used as an agent for improving the feel at the application of a hair cosmetic onto the hair or as a thickener for imparting a suitable viscosity to a hair cosmetic. Conventional thickeners include polyvinyl alcohol, cellulose derivatives, acrylic acid derivatives and the like. However, each of these thickeners cannot give a satisfactory feel when they are used alone, rather they impart a rough texture to the hair during the application or after overcome these disadvantages, a silicone excellent in water repellency, lubricating properties and glossiness, has been widely used. However, silicone oil is hardly soluble in nature and insoluble in highly polar solvents such as water. Thus, the application thereof is restricted. In order to solve these problems and to impart novel properties to a silicone oil, attempts have been made to modify a silicone oil by introducing long-chain alkyl groups, polyoxyalkylene groups, amino groups, carboxyl groups and epoxy groups thereto. Such an oily material as obtained above contains a polyoxyalkylene moiety at a high content so as to establish well balanced hydrophilic/hydrophobic properties. As a result, it is sometimes observed that the function as a silicone cannot fully be exerted. Further, there occurs another problem that the addition of such a silicone oil would deteriorate the setting-retention function of a hair cosmetic.

As described above, conventional modified silicones cannot fully satisfy the requirements as a cosmetic component, namely, the characteristics of a silicone oil (e.g., lubricating properties, water repellency, glossiness, the oil-free feel), adsorptivity on the hair or skin and solubility in highly polar solvents such as water.

SUMMARY OF THE INVENTION

Under these circumstances, the present inventors have conducted extensive studies. As a result, they have successfully found that a specific modified silicone having a poly(N-acylalkyleneimine) segment and an organopolysiloxane segment is excellent in solubility in various solvents, and sustains the desirable properties of silicone and thus a hair cosmetic comprising the modified silicone and a film-forming polymer exerts excellent functions, thus completing the present invention.

Accordingly, the present invention provides a hair cosmetic comprising the following components (a) and (b):

(a) a poly(N-acylalkyleneimine)-modified silicone having a poly(N-acylalkyleneimine) segment and an organopolysiloxane segment at a weight ratio of the poly(N-acylalkyleneimine) segment to the organopolysiloxane segment of from 1/20 to 20/1 and having a molecular weight of from 500 to 500,000, wherein said poly(N-acylalkyleneimine) segment comprises a repeating unit represented by the following formula (I):

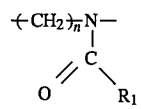

wherein $R_1$ represents a hydrogen atom, an alkyl group having 1 to 22 carbon atoms, a cycloalkyl group having 3 to 22 carbon atoms, an aralkyl group having 7 to 22 carbon atoms or an aryl group having 6 to 22 carbon atoms; and n is 2 or 3; and (b) a film-forming polymer.

DETAILED DESCRIPTION OF THE INVENTION

As the poly(N-acylalkyleneimine)-modified silicone to be used in the present invention, it is preferable to use a poly(N-acylalkyleneimine)-modified silicone wherein a poly(N-acylalkyleneimine) segment comprising a repeating unit of the formula (I):

wherein $R_1$ and n are as defined above; is bound to one or both of the ends and/or side chain of an organopolysiloxane segment via a group selected from among:

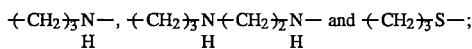

a weight ratio of the poly(N-acylalkyleneimine) segment to the organopolysiloxane segment is from 1/20 to 20/1; and the molecular weight is from 500 to 500,000.

In the groups represented by $R_1$ in formula (I), the alkyl group preferably has 1 to 10 carbon atoms, and more preferably has 1 to 6 carbon atoms; the cycloalkyl group preferably has 4 to 10 carbon atoms, and more preferably 4 to 6 carbon atoms; and the aryl group preferably has 6 to 12 carbon atoms, and more preferably 6 to 10 carbon atoms.

The poly(N-acylalkyleneimine)-modified silicone to be used in the present invention is a modified silicone wherein a poly(N-acylalkyleneimine) segment is bound to one or both of the ends and/or side chain of organopolysiloxane via the specific group as specified above. It may be synthesized, for example, in the following method.

First, a poly(N-acylalkyleneimine) segment comprising the repeating unit(s) represented by the above formula (I) may be obtained through ring-opening polymerization of a cyclic imino ether compound represented by the following formula (II):

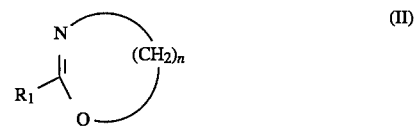

wherein $R_1$ and n are as defined above.

The cyclic imino ether compound represented by the above formula (II) may be selected from among 2-oxazolines or 2-oxazines. Specific examples thereof include 2-oxazoline, 2-methyl-2-oxazoline, 2-ethyl-2-oxazoline, 2-propyl-2-oxazoline, 2-butyl-2-oxazoline, 2-pentyl-2-oxazoline, 2-heptyl-2-oxazoline, 2-octyl-2-oxazoline, 2-nonyl-2-oxazoline, 2-decyl-2-oxazoline, 2-undecyl-2-oxazoline, 2-dodecyl-2-oxazoline, 2-tridecyl-2-oxazoline, 2-tetradecyl-2-oxazoline, 2-pentadecyl-2-oxazoline, 2-heptadecyl-2-oxazoline, 2-heptadecyl-2-oxazoline,2-octadecyl-2-oxazoline, 2-nonadecyl-2-oxazoline, 2-eicosyl-2-oxazoline, 2-heneicosyl-2-oxazoline, 2-docosyl-2-oxazoline, 2-benzyl-2-oxazoline, 2-phenyl-2-oxazoline, 2-naphthyl-2-oxazoline, 2-anthryl-2-oxazoline, 2-pyrenyl-2-oxazoline, 2-perylenyl-2-oxazoline, 2-cyclohexyl-2-oxazoline, 2-oxazine, 2-methyl-2-oxazine, 2-ethyl-2-oxazine, 2-propyl-2-oxazine, 2-butyl-2-oxazine, 2-pentyl-2-oxazine, 2-hexyl-2-oxazine, 2-heptyl-2-oxazine, 2-octyl-2-oxazine, 2-nonyl-2-oxazine, 2-decyl-2-oxazine, 2-undecyl-2-oxazine, 2-dodecyl 2-oxazine, 2-tridecyl-2-oxazine, 2-tetradecyl-2-oxazine, 2-pentadecyl-2-oxazine, 2-hexadecyl-2-oxazine, 2-heptadecyl-2-oxazine, 2-octadecyl-2-oxazine, 2-nonadecyl-2-oxazine, 2-eicosyl-2-oxazine, 2-heneicosyl-2-oxazine, 2-docosyl-2-oxazine, 2-benzyl-2oxazine, 2-phenyl-2-oxazine, 2-naphthyl-2-oxazine, 2-anthryl2-oxazine, 2-pyrenyl-2-oxazine, 2-perylenyl-2-oxazine and 2-cyclohexyl-2-oxazine.

Among the cyclic imino ether compounds, 2-oxazoline, 2-methyl-2-oxazoline, 2-ethyl-2-oxazoline, 2-propyl-2oxazoline, 2-butyl-2-oxazoline, 2-pentyl-2-oxazoline, 2oxazine, 2-methyl-2-oxazine, 2-ethyl-2-oxazine, 2-butyl-2oxazine, 2-pentyl-2-oxazine and 2-propyl-2-oxazine are preferred and 2-oxazoline, 2-methyl-2-oxazoline, 2-ethyl-2oxazoline, 2-oxazine, 2-methyl-2-oxazine and 2-ethyl-2oxazine are more preferred.

These cyclic imino ethers may be prepared by a method as disclosed, for example, in *Liebigs Ann. Chem.*, p 996–p 1009 (1974).

As a monomer to be subjected to ring-opening polymerization, either one of these compounds or a combination thereof may be used.

Ring-opining polymerization of the cyclic imino ether compound can be carried out in a method as disclosed, for example, in Angew. Chem., 78, 913 (1966), J. Polym. Sci., B, 5, 871 (1967), Polymer. J., 4, 87 (1973), Macromol. Chem. 12, 11 (1985).

Examples of a polymerization initiator to be used in the ring-opening polymerization of the above-mentioned cyclic imino ether include those disclosed in the above-cited references and specific examples thereof include alkyl toluenesulfonates, dialkyl sulfates, alkyl trifluoromethane-sulfonates and alkyl halides, though the present invention is not restricted thereto. Either one of these initiators or a mixture thereof may be used.

The poly(N-acylalkyleneimine) segment comprising the repeating unit(s) represented by the above-mentioned formula (I) can be obtained by the ring-opening polymerization of the cyclic imino ether compound represented by the above-mentioned formula (II) with the use of the above-mentioned polymerization initiator. The obtained segment may be either a homopolymer chain or a copolymer chain. The copolymer chain may be either a random copolymer chain or a block copolymer.

The molecular weight of the above-mentioned poly(N-acylalkyleneimine) segment may preferably range from 150 to 50,000, more preferably from 500 to 10,000. When the molecular weight thereof is less than 150, the properties of poly(N-acylalkyleneimine) may be deteriorated. On the other hand, a molecular weight exceeding 50,000 is undesirable since the production thereof may become difficult.

The poly(N-acylalkyleneimine)-modified silicone of the present invention can be obtained by reacting a compound having growing chain-end, which has been obtained by the ring-opening polymerization of the cyclic imino ether represented by the above formula (II), with an organopolysiloxane having a functional group capable of reacting therewith.

It is reported, for example, in Kobayashi and Saegusa, "Macromolecular Chemistry Supplement", 12, p. 11 (1985) that the above-mentioned compound having a growing chain-end is classified into two groups depending on the employed polymerization initiator, namely, ionic bond products (III) and covalent bond products (IV) respectively represented by the following general formulae (III) and (IV):

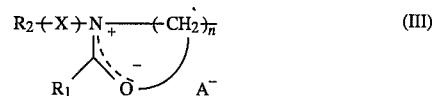  (III)

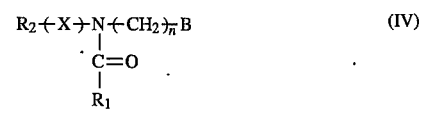  (IV)

wherein X represents a poly(N-acylalkyleneimine) chain; $R_1$ and n are as defined above; and $R_2$, A and B respectively represent the residues of initiators $R_2$-A and $R_2$-B.

Examples of the functional group capable of reacting with the above-mentioned compound having growing chain-end include primary and secondary amino groups, mercapto groups and metal carboxylates. Among these groups, primary amino groups and mercapto groups are particularly suitable therefor.

The molecular weight of an organopolysiloxane having primary amino groups in molecule preferably ranges from 300 to 300,000, more preferably from 800 to 80,000. It is preferred that 1 to 50 mols, more preferably 1 to 20 mols, of primary amino group(s) are contained per one molecule of the organopolysiloxane. Either a straight-chain organopolysiloxane or a branched one may be used in the present invention. When the molecular weight of the organopolysiloxane is less than 300, the functions as silicone cannot fully be exerted. When the molecular weight exceeds 300,000, on the other hand, it would set to gel and can hardly react. The primary amino groups contained in the organopolysiloxane may be incorporated at any site either in the main chain or in a side chain. Examples of the organopolysiloxane having primary amino groups are those represented by the following formulae (V) to (VIII):

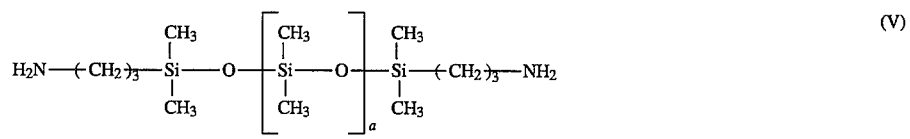  (V)

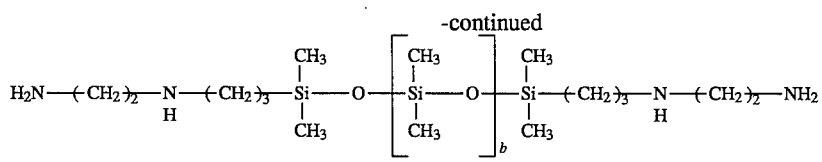

(VI)

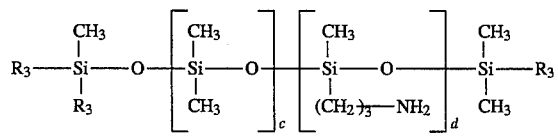

(VII)

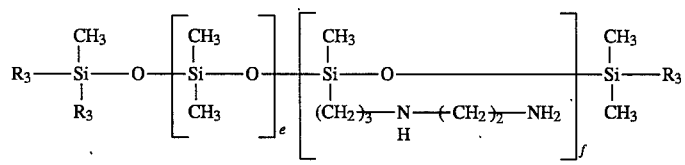

(VIII)

wherein $R_3$ represents a $CH_3$, $OCH_3$ or $OC_2H_5$ group; a is 1 to 20,000, preferably 5 to 1,000, more preferably 5 to 400; b is 1 to 20,000, preferably 5 to 1,000, more preferably 5 to 400; c is 1 to 20,000, preferably 5 to 1,000, more preferably 5 to 400; d is 1 to 1,000, preferably 1 to 100, more preferably 1 to 50; e is 1 to 20,000, preferably 5 to 1,000, more preferably 5 to 400; and f is 1 to 1,000, preferably 1 to 100, more preferably 1 to 50.

However, the organopolysiloxane to be used in the present invention is not restricted to those represented by the above formulae (V) to (VIII). Although these compounds may be synthesized by a well known method, marketed ones may be used therefor. Examples of marketed products thereof include FM3311, FM3321, FM3325, PS510 and PS513 (tradenames, products manufactured by Chisso Co.), X-22-161AS, X-22-161A, X-22-161B, X-22-161C, X-22-161Z, KF865, X-22-3680, KF864, X22-3801C, KF393, KF857, KF859, KF860, KF862, KF867, X-22-380D and KF-861 (tradenames, products manufactured by Shin-Etsu Silicone Co., Ltd.), SF8417, BY16-828, BY-16-849, BY16-850, BY16-859, BY16-872, BY16-853 and BY-16-853B (tradenames, products manufactured by Toray Silicone Co., Ltd.), and TSL9346, TSL9386, TSF4700, TSF4701, TSF4702, XF42-702 and XF42-703 (tradenames, products manufactured by Toshiba Silicone Co., Ltd.).

The molecular weight of the organopolysiloxane having mercapto groups in molecule preferably ranges from 300 to 300,000, more preferably from 800 to 80,000. It is preferred that 1 to 50 mols, more preferably 1 to 20 mols, of mercapto group(s) are contained per one molecule of the organopolysiloxane. Either a straight-chain organopolysiloxane or a branched one may be used. When the molecular weight of the organopolysiloxane is less than 300, the function as silicone cannot fully be exerted. When the molecular weight exceeds 300,000, on the other hand, the organopolysiloxane would set to gel and can hardly react. The mercapto groups contained in the organopolysiloxane may be incorporated at any site either in the main chain or in a side chain. Examples of the organopolysiloxane having mercapto groups are those represented by the following formulae (IX) and (X):

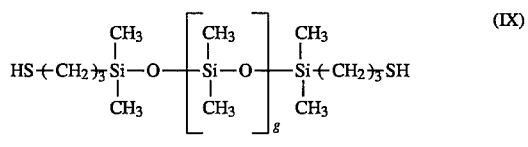

(IX)

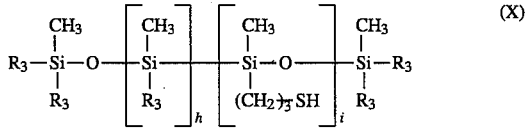

(X)

wherein $R_3$ is as defined above; g is 1 to 20,000, preferably 5 to 1,000, more preferably 5 to 400; h is 1 to 20,000, preferably 5 to 1,000, more preferably 5 to 400; and i is 1 to 1,000, preferably 1 to 100, more preferably 1 to 50.

However the organopolysiloxane to be used in the present invention is not restricted to those represented by the above formulae (IX) and (X). Although these compounds may be synthesized by a well known method, marketed ones may be used therefor. Examples of marketed products thereof include PS405 and RS927 (tradenames, products manufactured by Chisso Co.), X-22-980 (tradename, a product manufactured by Shin-Etsu Silicone Co., Ltd.), BY16-838A and BY16-838 (tradenames, products manufactured by Toray Silicone Co., Ltd.) and TSL9836, TSL9846, TSL9876 and TSL9886 (tradenames, products manufactured by Toshiba Silicone Co., Ltd.).

Ring-opening polymerization of the cyclic imino ether compound and the reaction between the organopolysiloxane having primary amino groups or mercapto groups and the reactive end(s) of the poly(N-acylalkyleneimine) obtained by ring-opening polymerization of the cyclic imino ether may be performed as follows.

A polymerization initiator is dissolved in a polar solvent (preferably, for example, acetonitrile, valeronitrile, dimethylformamide, dimethylacetamide, chloroform, methylene chloride, ethylene chloride), optionally together with other solvents, and heated to 40° to 150° C., preferably 60° to 100° C. Then a cyclic imino ether represented by the above-mentioned formula (II) is added thereto either at once or, in the case where a vigorous reaction occurs, dropwise, thereby initiating ring-opening polymerization. The progress of the polymerization may be monitored by determining the residual cyclic imino ether monomer by means of some analytical procedure such as gas chromatography. Even after the cyclic imino ether is completely consumed and the polymerization is completed, the growing chain-end(s) of the reaction product still sustains reactivity. Without isolating the resulting polymer from the solution, the polymer solution is then mixed with an organopolysiloxane having primary amino groups or mercapto groups in the molecule thereof, and the resulting mixture is allowed to react at 5° to 100° C., preferably 20° to 60° C. The mixing ratio may be arbitrarily selected. It is preferable to react from 0.1 to 1.1 molar equivalent of the poly(N-acylalkyleneimine) per mole of the primary amino or mercapto group in the organopolysiloxane. When the amount of the poly(N-acylalkyleneimine) is less than 0.1 molar equivalent, the desirable functions of the poly(N-acylalkyleneimine) to be used in the present invention are difficult to obtain due to a low modification ratio. On the other hand, it is unnecessary to use such a large amount of the poly(N-acylalkyleneimine) as exceeding 1.1 molar equivalent.

It is undesirable if water is present in the reaction system since the reactive end of the poly(N-acylalkyleneimine) would react with the water to thereby form, for example, the corresponding alcohol in this case. Thus it is preferable to remove water from the reaction system almost completely. Therefore, it is recommended to perform the reaction under an inert gas (for example, nitrogen gas) atmosphere.

Thus, a block copolymer wherein a poly(N-acylalkyleneimine) segment is bound to an end of the organopolysiloxane is obtained when a compound represented by the formula (V), (VI) or (IX) is used as an organopolysiloxane. When a compound represented by the formula (VII), (VIII) or (X) is used, alternately, a graft copolymer wherein a poly(N-acylalkyleneimine) segment is bound to a side chain of the organopolysiloxane is obtained.

The poly(N-acylalkyleneimine)-modified silicone to be used in the present invention varies in state, i.e., from a viscous oil to a solid resin depending on the employed organopolysiloxane segment, poly(N-acylalkyleneimine) segment and the combination of these segments. The characteristics of the present invention can be exerted when the weight ratio of the poly(N-acylalkyleneimine) segment to the organopolysiloxane segment falls within a range of 1/20 to 20/1, still preferably 1/10 to 5/1. From a practical viewpoint, the molecular weight of the poly(N-acylalkyleneimine)-modified silicone preferably range from 500 to 500,000, more preferably from 1,000 to 100,000. The molecular weight can be determined by gel permeation chromatography (GPC).

The content of the poly(N-acylalkyleneimine)-modified silicone in the hair cosmetic of the present invention is not particularly restricted. It may preferably range from 0.01 to 10% by weight (the same will apply hereinafter), preferably from 0.1 to 5% by weight, based on the total weight of the composition.

The film-forming polymer to be used in the present invention may be selected from among those cited below.
(1) polyvinyl pyrrolidone polymer compounds:
(1-1) polyvinyl pyrrolidone:

As polyvinyl pyrrolidone to be used in the present invention, those having a molecular weight of 8,000 to 630,000. Examples of marketed products thereof include Luviskol K12 and K30 (tradenames, products manufactured by BASF Co.) and PVP K15 and K30 (tradenames, products manufactured by GAF Co.).
(1-2) polyvinyl pyrrolidone/vinyl acetate copolymer:

Specific examples thereof include those disclosed, for example, in U.S. Pat. No. 3,171,784. Examples of marketed products thereof include Luviskol VA28 and VA73 (tradenames, products manufactured by BASF Co.) and PVP/VA E-735 and S-630 (tradenames, products manufactured by GAF Co.).
(1-3) polyvinyl pyrrolidone/vinyl acetate/vinyl propionate terpolymer:

Specific examples thereof include those disclosed, for example, in JP-A-59-217708 (the term "JP-A" as used herein means an "unexamined published Japanese patent Application"). Examples of marketed products thereof include Luviskol VAP343 (tradename, a product manufactured by BASF Co.).
(1-4) polyvinyl pyrrolidone/alkylamino acrylate copolymer:

Examples of marketed products thereof include Luviflex (tradename, a product manufactured by BASF Co.) and Copolymer 845, 937 and 958 (tradenames, products manufactured by GAF Co.).
(1-4) polyvinyl pyrrolidone/acrylate/(meth)acrylic acid copolymer:

Examples of marketed products thereof include Luviflex VBM 35 (tradename, a product manufactured by BASF Co.).
(1-5) polyvinyl pyrrolidone/alkylamino acrylate/vinyl caprolactam copolymer:

Specific examples thereof include those disclosed, for example, in JP-A-58-49715. Examples of marketed products thereof include Copolymer VC-713 (tradename, a product manufactured by GAF Co.).
(2) Acidic vinyl ether polymer compounds:
(2-1) Methyl vinyl ether/alkylmaleic anhydride alkyl half ester copolymer:

Specific examples thereof include those disclosed, for example, in U.S. Pat. No. 2,957,838. Examples of marketed products thereof include Gantrez ES-225, ES-425 and Sp-215 (tradenames, products manufactured by GAF Co.).
(3) Acidic polyvinyl acetate compounds:
(3-1) Vinyl acetate/crotonic acid copolymer:

Examples of marketed products thereof include Resyn 28-1310 (tradename, a product manufactured by National Starch Co.) and Luviset CA 66 (tradename, a product manufactured by BASF Co.).
(3-2) Vinyl acetate/crotonic acid/vinyl neodecanoate copolymer:

Specific examples thereof include those disclosed, for example, in JP-A-54-155185. Examples of marketed products thereof include Resyn 28-2930 (tradename, a product manufactured by National Starch Co.).
(3-3) Vinyl acetate/crotonic acid/vinyl propionate copolymer:

Specific examples thereof include those disclosed, for example, in FR-1222944, FR-1580545, FR-2265782, FR-2265781 and FR-1564110. Examples of marketed products thereof include Luviset CAP (tradename, a product manufactured by BASF Co.).
(4) Acidic acryl polymer compounds:
(4-1) (Meth)acrylic acid/(meth)acrylate copolymer:

Specific examples thereof include those disclosed, for example, in JP-A-44-31238. Examples of marketed products thereof include PLASCIZE L53p (tradename, a product manufactured by Goo kagaku K.K.) and Daiahold (tradename, a product manufactured by Mitsubishi petrochemical Co., Ltd.).
(4-2) Acrylic acid/alkyl acrylate/alkylacrylamide copolymer:

Specific examples thereof include those disclosed, for example, in JP-A-49-14647. Examples of marketed products thereof include Ultrahold 8 (tradename, a product manufactured by BASF Co.) and Amphormer V-42 (tradename, a product manufactured by National Starch Co.).

(5) Amphoteric acryl polymer compounds:
(5-1) Dialkylaminoethyl (meth)acrylate/alkyl (meth)acrylate copolymer:

Specific examples thereof include those disclosed, for example, in JP-A-56-92809. Examples of marketed products thereof include Yukaformer M-75 and SM (tradenames, products manufactured by Mitsubishi petrochemical Co., Ltd.).

(5-2) Hydroxypropyl acrylate/butylaminoethyl methacrylate/acrylic acid octylamide copolymer:

Specific examples thereof include those disclosed, for example, in-JP-A-49-14647 and JP-A-1-275518. Examples of marketed products thereof include Amformer 28-4910 (tradenames, a product manufactured by National Starch Co.).

(6) Basic acryl polymer compounds:
(6-1) Acrylamide acrylester tetracopolymers:

Specific examples thereof include those disclosed, for example, in JP-A-2-180911.

(7) Cellulose derivatives:
(7-1) Cationic cellulose derivative:

Specific examples thereof include those disclosed, for example, in FR-1492597. Examples of marketed products thereof include Celquat H-100 and L-200 (tradenames, products manufactured by National Starch Co.).

(8) Chitin derivatives and chitosan derivatives:
(8-1) Hydroxypropyl chitosan:

Specific examples thereof include those disclosed, for example, in JP-A-3-109310. Examples of marketed products thereof include Chitofilmer (tradename, a product manufactured by ICHIMARU PHARCOS CO., LTD.).

(8-2) Carboxymethyl chitin:
(8-3) Carboxymethyl chitosan:

Among these film-forming polymers, those selected from among (meth)acrylic acid polymers (i.e., the acidic acryl polymer compounds (4), the amphoteric acryl polymer compounds (5) and the basic acryl polymer compounds (6)), polyvinyl pyrrolidone polymers (i.e., the polyvinyl pyrrolidone polymer compounds (1)) and those having a sugar skeleton (i.e., the cellulose derivatives (7) and the chitin and chitosan derivatives (8)) are particularly preferable. The content of the film-forming polymer in the hair cosmetic of the present invention may preferably range from 0.05 to 20% by weight, more preferably from 0.1 to 10% by weight, based on the total weight of the composition.

In addition to the above-mentioned poly(N-acylalkyleneimine)-modified silicone and film-forming polymer, the hair cosmetic of the present invention may further contain solvents such as water and ethanol and almost any of components commonly employed in the art (for example, surfactants, oily substances, polyhydric alcohols, various medical components, preservatives, perfumes). Namely, the components of the hair cosmetic of the present invention may be appropriately selected from among the above-mentioned ones depending on the object, purpose and form of the product.

For example, a surfactant may be selected from among straight-chain or branched alkylbenzenesulfonates, ethylene oxide and/or propylene oxide adducts of alkyl or alkenyl ether sulfates, olefinsulfonates, alkanesulfonates, saturated or unsaturated fatty acid salts, ethylene oxide and/or propylene oxide adducts of alkyl or alkenyl ether carboxylates, α-sulfo fatty acid salt esters, amino acid surfactants, phosphate type surfactants, sulfosuccinic acid surfactants, sulfonic acid amphoteric surfactants, betaine amphoteric surfactants, alkylamine oxides, cationic surfactants, polyoxyalkyl or alkenyl ethers, polyoxyalkyl phenyl ethers, higher fatty acid alkanolamides or alkylene oxide adducts, esters of polyhydric alcohols with fatty acids, esters of sorbitol with fatty acids, esters of sucrose with fatty acids and ethers of higher alcohols with sugars. The content of the surfactant in the hair cosmetic of the present invention may preferably range from 0.01 to 60% by weight, more preferably 0.05 to 20% by weight, based on the total weight of the composition.

An oily component may be selected from among higher fatty acids such as stearic acid; higher alcohols such as cetanol; solid fats such as cholesterol, vaseline, cholesteryl isostearate and sphingolipids; and liquid oils such as squalane, jojoba oil and other silicone derivatives. A polyhydric alcohol may be selected from among glycerol, 1,3-butylene glycol, propylene glycol, dipropylene glycol, polyethylene glycol and sorbitol.

As other components, those selected from among, for example, pearling agents; perfumes; dyes; UV absorbers; antioxidants; bactericides such as triclosan and trichlorocarbane; antiinflammatory agents such as potassium glycyrrhetinate and tocopherol acetate; anti-dandruff agents such as zinc pyrithione and octopirox; and preservatives such as methylparaben and butylparaben may be arbitrarily added so long as the effects of the present invention are not deteriorated thereby.

To further illustrate the present invention in greater detail, and not by way of limitation, the following Synthesis Examples and Examples will be given.

Unless otherwise noted, all percentages given in the following Synthesis Examples and Examples are by weight.

SYNTHESIS EXAMPLE 1

A mixture comprising 13.03 g (0.070 mol) of methyl p-toluenesulfonate (methyl tosylate), 70 g (0.82 mol) of 2-methyl-2-oxazoline, 10 ml of acetonitrile and 30 ml of chloroform was heated under reflux for 6 hours. Thus a poly(N-acetylethyleneimine) polymer having reactive ends (molecular weight: 1,000) was synthesized. To the reaction mixture, a solution of 31.8 g of polydimethylsiloxane substituted with 3-aminopropyl at both ends (FM3311, tradename, a product manufactured by Chisso Co.; molecular weight: 1,000) dissolved in 50 ml of chloroform was added and reaction was proceeded at 55° C. for 24 hours. After distilling off the solvent under reduced pressure, a block copolymer of polydimethylsiloxane having poly(N-acetylethyleneimine) chains bound to both the ends (molecular weight: 3,000) was obtained. This copolymer was in the form of a pale yellow, brittle solid.

SYNTHESIS EXAMPLE 2

A mixture comprising 1.45 g ($7.8 \times 10^{-3}$ mol) of methyl tosylate, 7.8 g (0.033 mol) of 2-n-undecyl-2-oxazine and 10 ml of dimethylacetamide was maintained at 100° C. for 24 hours to thereby synthesize poly(N-n-dodecanoylpropyleneimine) (molecular weight: 1,000). To the reaction mixture, a solution of 38.9 g of polydimethylsiloxane substituted with 3-aminopropyl at both the ends (FM3325, tradename, a product manufactured by Chisso Co.; molecular weight: 10,000) dissolved in 50 ml of chloroform was added and the resulting mixture was refluxed for 72 hours. After re-precipitating from methanol, the obtained residue was dried under reduced pressure. Thus a polymer having a molecular weight of 12,000 was obtained as a yellow viscous liquid.

EXAMPLE 1

With the use of the poly(N-acylalkyleneimine)-modified silicones obtained in the above Synthesis Examples 1 and 2, hair mists of compositions listed in the following Table 1 were prepared.

Each hair mist thus obtained was applied to the hair and the setting-retention function and slipperiness were evaluated by the methods as specified below. Table 1 shows the results.

<Test method>

(1) Setting-retention function:

A hair bundle (length: 18 cm, weight: 1.5 g) was moistened with water and dried with towel. After applying 2 g of a hair mist, the hair bundle was wound round a rod of 2 cm in diameter and spontaneously dried. After drying, the hair bundle thus curled was taken off from the rod and suspended in an equilibrated chamber (20° C., 98% RH) for 30 minutes. Next, the elongation of the curled hair was observed by ten skilled panelists and the setting-retention function of the hair mist Was evaluated based on the following criteria.

A: Very good

B: Good

C: Moderate

D: Somewhat poor

E: Very poor (2) Slipperiness

A hair bundle (length: 18 cm, weight: 10 g) was moistened with water and dried with towel. After applying 0.2 g of a hair mist, the hair bundle was spontaneously dried. Then the feel of the hair was evaluated by ten skilled panelists based on the following criteria.

A: Very good

B: Good

C: Moderate

D: Somewhat poor

E: Very poor

TABLE 1

| Hair Mist Composition | Product of the Invention | |
|---|---|---|
| | A (% by weight) | B (% by weight) |
| Modified silicone of Synthetic Example 1 | 1.5 | — |
| Modified silicone of Synthetic Example 2 | — | 1.5 |
| Amphoteric polymer (Yukaformer M-75)*1 | 5.0 | 5.0 |
| Nonionic surfactant (glyceryl isostearate) | 0.5 | 0.5 |
| Perfume | trace | trace |
| Ethanol | appropriate amount | appropriate amount |
| Total | 100.0 | 100.0 |
| Evaluation: | | |
| Setting-retention function | A | B |
| Slipperiness | B | A |

Note: *1: A product manufactured by Mitsubishi Petrochemical Co., Ltd.

EXAMPLE 2

A hair blowing agent was produced by blending the following components.

| Component | Amount (% by weight) |
|---|---|
| Poly(N-acylalkyleneimine)-modified silicone of Synthetic Example 2 | 0.5 |
| Amphoteric polymer (Yukaformer M-75) | 0.5 |
| Perfume | trace |
| Ethanol | 30.0 |
| Purified water | appropriate amount |
| Total | 100.0 |

EXAMPLE 3

A hair foam was produced by blending the following components.

| Component | Amount (% by weight) |
|---|---|
| Poly(N-acylalkyleneimine)-modified silicone of Synthetic Example 1 | 1.0 |
| Chitin liquid (a product of ICHIMARU PHARCOS CO., LTD.) | 5.0 |
| Nonionic surfactant (Softanol, tradename a product manufactured by Nippon Shokubai K.K.) | 1.0 |
| Perfume | trace |
| Liquefied petroleum gas | 10.0 |
| Purified water | appropriate amount |
| Total | 100.0 |

EXAMPLE 4

A hair spray was produced by blending the following components.

| Component | Amount (% by weight) |
|---|---|
| Poly(N-acylalkyleneimine)-modified silicone of Synthetic Example 1 | 1.5 |
| Nonionic surfactant (Luviskol VA37, tradename, a product manufactured by BASF Co.) | 5.0 |
| Perfume | trace |
| Liquefied petroleum gas | 50.0 |
| Ethanol | appropriate amount |
| Total | 100.0 |

EXAMPLE 5

A hair setting lotion was produced by blending the following components.

| Component | Amount (% by weight) |
|---|---|
| Poly(N-acylalkyleneimine)-modified silicone of Synthetic Example 2 | 1.0 |
| Amphoteric polymer (Yukaformer M-75) | 2.0 |
| Ethanol | appropriate amount |
| Purified water | 10.0 |

| Component | Amount (% by weight) |
| --- | --- |
| Perfume | trace |
| Total | 100.0 |

The hair cosmetic of the present invention, which comprises a specific poly(N-acylalkyleneimine)-modified silicone in combination with another film-forming polymer, is effective in imparting a natural gloss, smoothness, flexibility, smooth-combing properties and water repellency to the hair without deteriorating the hair setting retention function.

While the invention has been described in detail and with reference to specific examples thereof, it will be apparent to one skilled in the art that various changes and modifications can be made therein without departing from the spirit and scope thereof.

What is claimed is:

1. A hair cosmetic comprising:

(a) from 0.01 to 10% by weight of a poly(N-acylalkyleneimine-organopolysiloxane block or graft copolymer having a poly(N-acylalkyleneimine) segment and an organopolysiloxane segment, said poly(N-acylalkyleneimine) segment comprising a repeating unit of the formula (I):

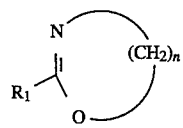

wherein $R_1$ represents a hydrogen atom, an alkyl group having 1 to 22 carbon atoms, a cycloalkyl group having 3 to 22 carbon atoms, an aralkyl group having 7 to 22 carbon atoms or an aryl group having 6 to 22 carbon atoms, and n is 2 or 3; and said organopolysiloxane segment having a formula selected from the group consisting of formulae (V) to (X):

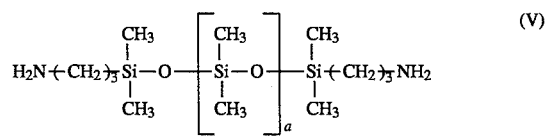

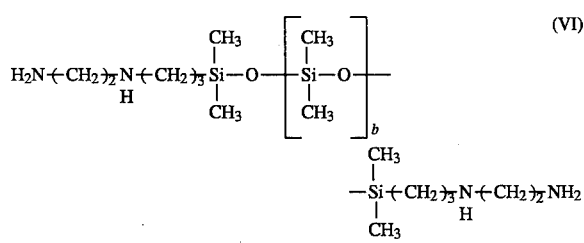

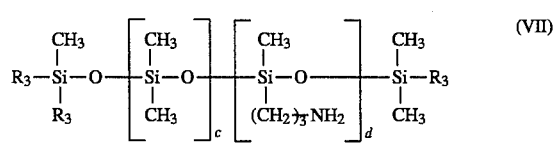

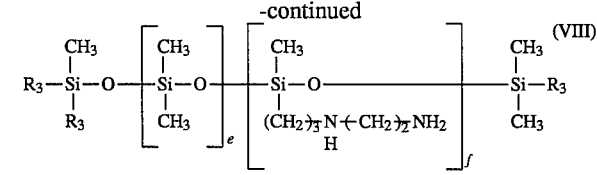

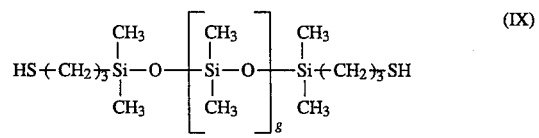

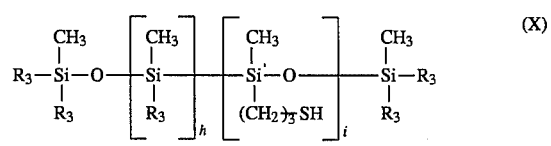

wherein $R_3$ represents a $CH_3$, $OCH_3$ or $OC_2H_5$; said poly(N-acylalkyleneimine) segment and said organopolysiloxane segment being present in a weight ratio of from 1/20 to 20/1, and said block or graft copolymer having a molecular weight of from 500 to 500,000, in which said poly(N-acylalkyleneimine) segment has a molecular weight of from 150 to 50,000 and said organopolysiloxane segment has a molecular weight of from 300 to 300,000, and (b) from 0.05 to 20% by weight of a film-forming polymer selected from the group consisting of polyvinyl pyrrolidone polymer compounds, acidic vinyl ether polymer compounds, acidic polyvinyl acetate compounds, acidic acryl polymer compounds, amphoteric acryl polymer compounds, basic acryl polymer compounds, cellulose derivatives, chitin derivatives and chitosan derivatives.

2. The hair cosmetic of claim 1, wherein said film-forming polymer is selected from the group consisting of polyvinyl pyrrolidone polymer compounds, amphoteric acryl polymer compounds, basic acryl polymer compounds, chitin derivatives and chitosan derivatives.

3. The hair cosmetic of claim 1, wherein said organopolysiloxane segment has a formula selected from the group consisting of formula (V), formula (VI), formula (VII) and formula (VIII).

4. The hair cosmetic of claim 3, wherein said poly(N-acylalkyleneimine) segment and said organopolysiloxane segment are present in a weight ratio from 1/10 to 5/1.

5. The hair cosmetic of claim 4, wherein said block or graft polymer has a molecular weight of from 1,000 to 100,000.

6. The hair cosmetic of claim 1, wherein said poly(N-acylalkyleneimine) segment has a molecular weight of from 500 to 10,000, and said organopolysiloxane segment has a molecular weight of from 800 to 80,000.

7. The hair cosmetic of claim 1, wherein a, b, c and e are each a number of from 5 to 1,000, and d and f are each a number of 1 to 100.

8. The hair cosmetic of claim 7, wherein a, b, c and e are each a number of from 5 to 400, and d and f are each a number of from 1 to 50.

9. The hair cosmetic of claim 8, wherein said organopolysiloxane segment has the formula (V).

10. The hair cosmetic of claim 9, wherein said poly(N-acylalkyleneimine)-organopolysiloxane block or graft copolymer is present in an amount of from 0.1 to 5% by weight of the total weight of the composition.

11. The hair cosmetic of claim 1, wherein said poly(N-acylalkyleneimine)-organopolysiloxane block or graft copolymer is present in an amount of from 0.1 to 5% by weight of the total weight of the composition.

12. The hair cosmetic of claim 1, wherein said poly(N-acylalkyleneimine)-organopolysiloxane block or graft copolymer is prepared by the steps of:

(i) ring-opening polymerizing a cyclic imino ether compound represented by the following formula (II):

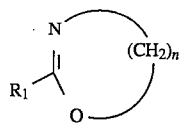

(II)

wherein $R_1$ represents a hydrogen atom, an alkyl group having 1 to 22 carbon atoms, a cycloalkyl group having 3 to 22 carbon atoms, an aralkyl group having 7 to 22 carbon atoms or an aryl group having 6 to 22 carbon atoms, and n is 2 or 3; and (ii) polymerizing of a reaction product of the step (i) with one molar equivalent of an organopolysiloxane having a formula selected from the group consisting of formulae (V) to (x):

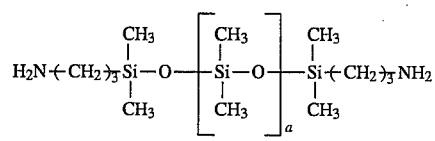

(V)

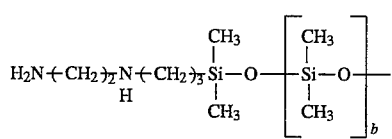

(VI)

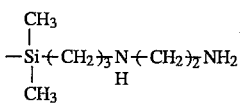

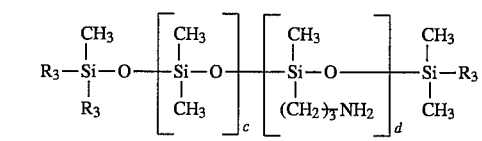

(VII)

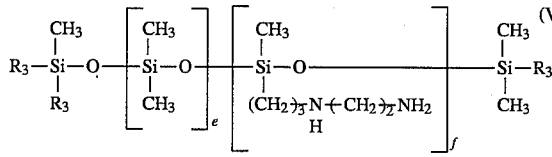

(VIII)

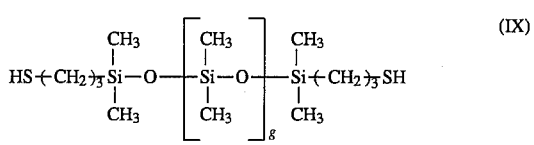

(IX)

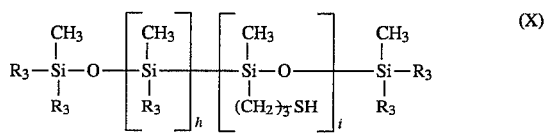

(X)

wherein $R_3$ represents a $CH_3$, $OCH_3$ or $OC_2H_5$, and from 0.1 to 1.1 molar equivalents of said reaction product of the step (i) is reacted per mole of primary amino or mercapto groups of said organopolysiloxane; such that said poly(N-acylalkyleneimine) segment has a molecular weight of from at least 150 and said organopolysiloxane segment has a molecular weight of from 300 to 300,000, said poly(N-acylalkyleneimine) segment and said organopolysiloxane segment are present in a weight ratio of from 1/20 to 20/1, and said block or graft copolymer has a molecular weight of from 500 to 500,000.

13. The hair cosmetic of claim 1, wherein said film-forming polymer is selected from the group consisting of polyvinyl pyrrolidone, a polyvinyl pyrrolidone/vinyl acetate copolymer, a polyvinyl pyrrolidone/vinyl acetate/vinyl propionate terpolymer, a polyvinyl pyrrolidine/alkylamino acrylate copolymer, a polyvinyl pyrrolidone/acrylate/(meth)acrylic acid copolymer, a polyvinyl pyrrolidone/alkylamino acrylate/vinyl caprolactam copolymer, a methyl vinyl ether/alkylmaleic anhydride alkyl half ester copolymer, a vinyl acetate/crotonic acid copolymer, a vinyl acetate/crotonic acid/vinyl neodecanoate copolymer, a vinyl acetate/crotonic acid/vinyl propionate copolymer, a (meth)acrylic acid/(meth) acrylate copolymer, an acrylic acid/alkyl acrylate/alkylacrylamide copolymer, a dialkylaminoethyl (meth) acrylate/alkyl(meth)acrylate copolymer, a hydroxypropyl acrylate/butylaminoethyl methacrylate/acrylic acid octylamide copolymer, an acrylamide acrylester tetracopolymer, a cationic cellulose, hydroxypropyl chitosan, carboxymethyl chitin and carboxymethyl chitosan.

* * * * *

UNITED STATES PATENT AND TRADEMARK OFFICE
CERTIFICATE OF CORRECTION

PATENT NO. : 5,472,689

DATED : December 5, 1995

INVENTOR(S) : Yoshiaki Ito

It is certified that error appears in the above-indentified patent and that said Letters Patent is hereby corrected as shown below:

Column 13, line 32,

" 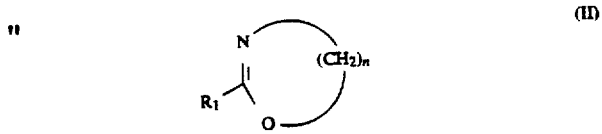 (II) "

should read

-- 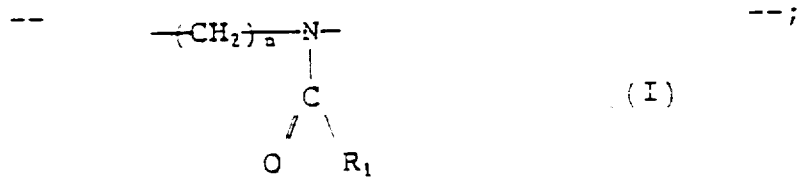 --;

(I)

line 47,

" 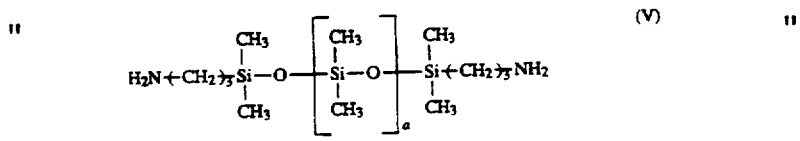 (V) "

UNITED STATES PATENT AND TRADEMARK OFFICE
CERTIFICATE OF CORRECTION

PATENT NO. : 5,472,689

DATED : December 5, 1995

INVENTOR(S) : Yoshiaki Ito

It is certified that error appears in the above-indentified patent and that said Letters Patent is hereby corrected as shown below:

should read

-- 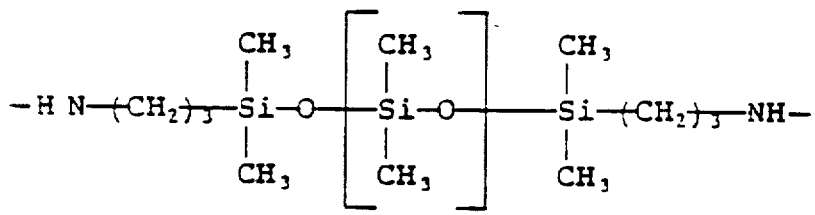 --;

line 53,

" 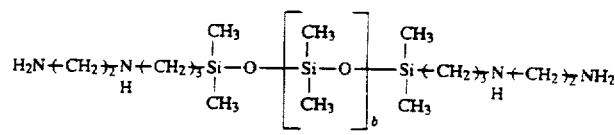 "

should read

-- 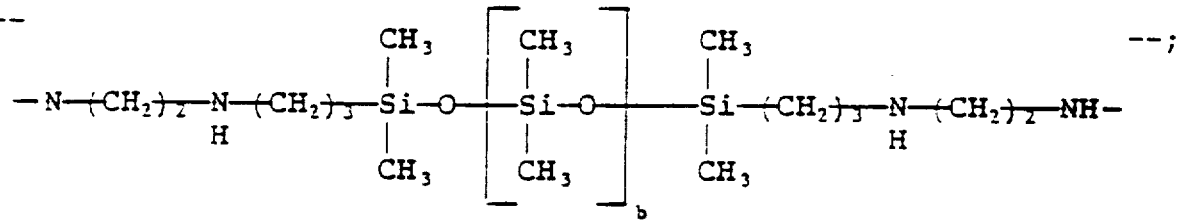 --;

UNITED STATES PATENT AND TRADEMARK OFFICE
CERTIFICATE OF CORRECTION

PATENT NO. : 5,472,689
DATED : December 5, 1995
INVENTOR(S) : Yoshiaki Ito

It is certified that error appears in the above-indentified patent and that said Letters Patent is hereby corrected as shown below:

line 63,

" 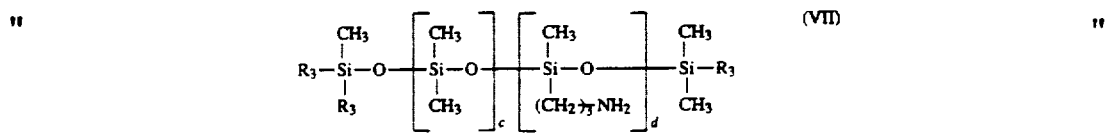 "

should read

-- 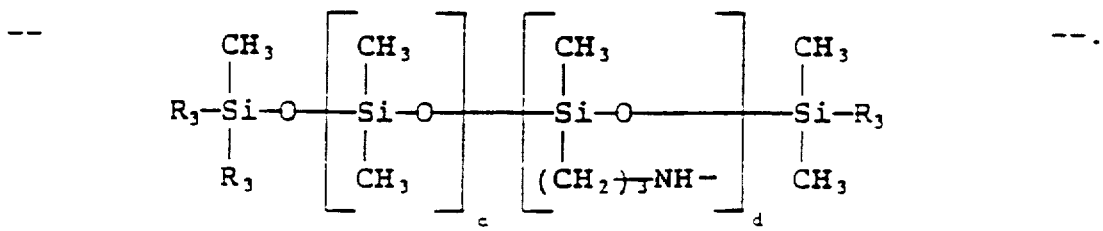 --.

Column 14, line 5,

" 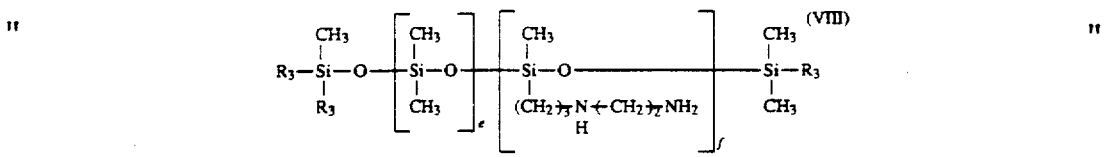 "

UNITED STATES PATENT AND TRADEMARK OFFICE
CERTIFICATE OF CORRECTION

PATENT NO. : 5,472,689

DATED : December 5, 1995

INVENTOR(S) : Yoshiaki Ito

It is certified that error appears in the above-indentified patent and that said Letters Patent is hereby corrected as shown below:

should read

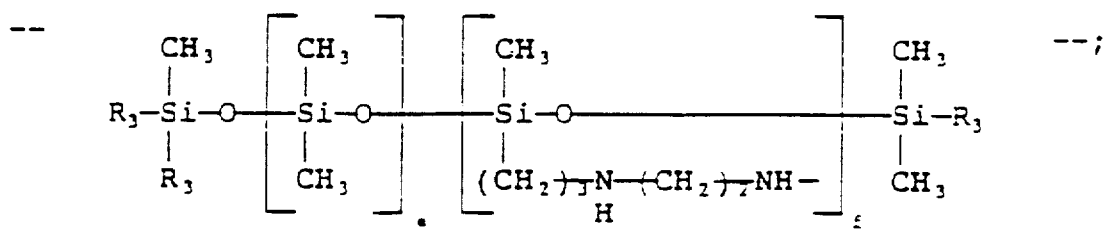

line 10,

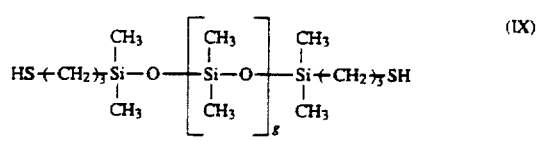

should read

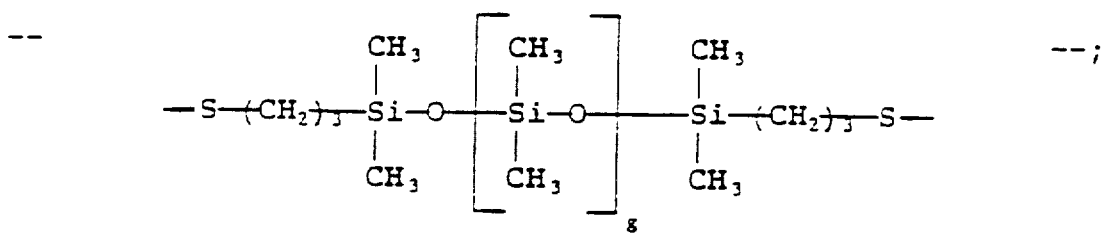

UNITED STATES PATENT AND TRADEMARK OFFICE
CERTIFICATE OF CORRECTION

PATENT NO. : 5,472,689
DATED : December 5, 1995
INVENTOR(S) : Yoshiaki Ito

It is certified that error appears in the above-indentified patent and that said Letters Patent is hereby corrected as shown below:

line 16,

" 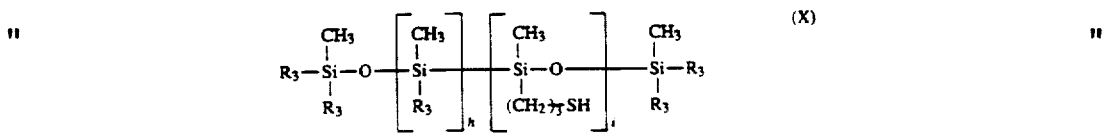 "

should read

-- 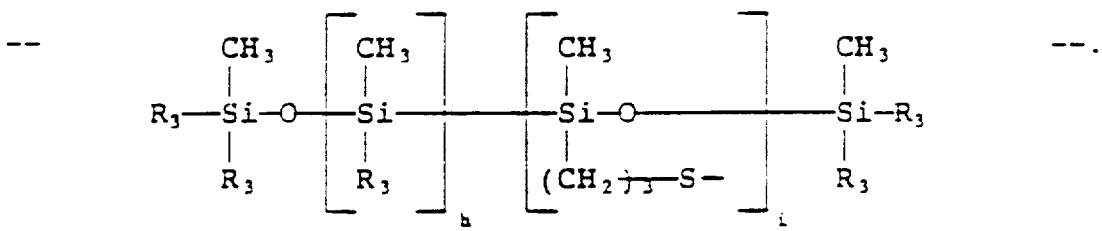 --.

Column 15, line 26, "(x)" should read --(X)--.

Signed and Sealed this

Fifteenth Day of October, 1996

Attest:

BRUCE LEHMAN

Attesting Officer     Commissioner of Patents and Trademarks